(12) United States Patent
Lehmann

(10) Patent No.: US 10,822,287 B2
(45) Date of Patent: Nov. 3, 2020

(54) METHOD FOR PRODUCING A BIOLOGICALLY ACTIVE, MICROORGANISM-CONTAINING AQUEOUS SOLUTION OR SUSPENSION

(71) Applicant: Stephan Lehmann, Berlin (DE)

(72) Inventor: Stephan Lehmann, Berlin (DE)

(*) Notice: Subject to any disclaimer, the term of this patent is extended or adjusted under 35 U.S.C. 154(b) by 549 days.

(21) Appl. No.: 15/173,784

(22) Filed: Jun. 6, 2016

(65) Prior Publication Data

US 2016/0362344 A1 Dec. 15, 2016

(30) Foreign Application Priority Data

Jun. 10, 2015 (DE) .......... 10 2015 109 233

(51) Int. Cl.
| | |
|---|---|
| *C05F 9/04* | (2006.01) |
| *C02F 3/34* | (2006.01) |
| *C05G 5/23* | (2020.01) |
| *C05G 5/27* | (2020.01) |
| *A61K 36/06* | (2006.01) |
| *C02F 3/00* | (2006.01) |
| *C02F 103/00* | (2006.01) |

(52) U.S. Cl.
CPC ............ *C05F 9/04* (2013.01); *A61K 36/06* (2013.01); *C02F 3/00* (2013.01); *C02F 3/348* (2013.01); *C05G 5/23* (2020.02); *C05G 5/27* (2020.02); *C02F 2103/007* (2013.01); *C02F 2209/02* (2013.01); *C02F 2209/04* (2013.01); *C02F 2209/06* (2013.01); *C02F 2209/22* (2013.01); *Y02A 40/20* (2018.01); *Y02P 20/145* (2015.11); *Y02W 30/40* (2015.05)

(58) Field of Classification Search
None
See application file for complete search history.

(56) References Cited

U.S. PATENT DOCUMENTS 8,173,185 B2 * 5/2012 Hanada .............. A23L 27/50
426/46

FOREIGN PATENT DOCUMENTS

| DE | 10163001 | 7/2003 |
|---|---|---|
| EP | 1010754 | 6/2000 |
| WO | 2012122530 | 9/2012 |

OTHER PUBLICATIONS

Siddiqui et al. 2009. Bio-potential of compost tea from agro-waste to suppress *Choanephora cucurbitarum* L. the causal pathogen of wet rot of okra. Biological control, vol. 49, pp. 38-44; published online Dec. 11, 2008 (Year: 2009).*

US Legal. Ambient temperature law and legal definition. Copyright 1997-2016, 4 Pages (Year: 1997).*
Jolanum et al. 2010. Novel bulking agent from Clay residue for food waste composting. Bioresource Technology, vol. 101, pp. 4484-4490. (Year: 2010).*
Garden Tea company. 2011, 15 Pages. (Year: 2011).*
Scheuerell et al. 2002. Literature Review, Compost Tea: Principles and Prospects For Plant Disease Control. Compost signs and utilization, vol. 10, No. 4, pp. 313-338. (Year: 2002)*
Judith. 2011, From Char Biological. Compost Tea and Biochar 3 Pages. Printed Aug. 6, 2018. (Year: 2011).*
Alvarez, Rene, Saul Villca, and Gunnar Liden. "Biogas production from llama and cow manure at high altitude." Biomass and Bioenergy 30.1 (2006): 66-75. (Year: 2006).*
Garff, Marianna, et al. "Psychrophilic anaerobic digestion of guinea pig manure in low-cost tubular digesters at high altitude." Bioresource technology 102.10 (2011): 6356-6359. (Year: 2011).*
Wei, Suzhen, et al. "Psychrophilic anaerobic co-digestion of highland barley straw with two animal manures at high altitude for enhancing biogas production." Energy conversion and management 88 (2014): 40-48. (Year: 2014).*
Sreekrishnan, T. R., Sangeeta Kohli, and Vineet Rana. "Enhancement of biogas production from solid substrates using different techniques—a review." Bioresource technology 95.1 (2004): 1-10. (Year: 2004).*
Fang, Cheng, Kanokwan Boe, and Irini Angelidaki. "Anaerobic co-digestion of desugared molasses with cow manure; focusing on sodium and potassium inhibition." Bioresource technology 102.2 (2011): 1005-1011. (Year: 2011).*
Permaculture News webpage, entitled How to Prepare a Beneficial Microorganisms Mixture (2012), accessed at: https://www.permaculturenews.org/2012/02/04/how-to-prepare-a-beneficial-microorganism-mixture/ (Year: 2012).*
Emvereniging webpage, entitled Things to Know about Effective Microorganisms (2008), accessed at: https://www.emvereniging.nl/things-to-know-about-effective-microorganisms-em/ (Year: 2008).*
Organic Gardener's Pantry webpage, entitled Making Activated EM (2011), accessed at: https://web.archive.org/web/20111203165800/https://www.gardenerspantry.ca/great-tips-and-videos/activated-em.html (2011) (Year: 2011).*
Kyan, Takashi, et al. "Kyusei nature farming and the technology of effective microorganisms." Bankok, TH, Interncional Nature Farming Research Center, Atami, Japan and Asia Pacific Natural Agriculture Network 44p (1999). (Year: 1999).*
Ting, Adeline Su Yien, et al. "Investigating metal removal potential by Effective Microorganisms (EM) in alginate-immobilized and free-cell forms." Bioresource technology 147 (2013): 636-639. (Year: 2013).*
Elaine R. Ingham, PhD, "The Compost Tea Brewing Manual", Fifth Edition, Soil Foodweb Incorporated, Apr. 2005.

(Continued)

*Primary Examiner* — Robert J Yamasaki
(74) *Attorney, Agent, or Firm* — Sand, Sebolt & Wernow Co., LPA

(57) ABSTRACT

A method for producing a biologically active, microorganism-containing aqueous solution or suspension including steps of the provision of water, the optional addition of a fine-grained mineral or organic material to the water and mixing of this materials into the water in order to obtain a suspension, the addition of compost to the suspension, and resting the suspension in an airtight environment for at least one week at a temperature of less than 15° C. This method allows the production of a biologically active, microorganism-containing solution or suspension which can be added to natural bodies of water or to soil, and may be used for external and internal application in humans and animals.

20 Claims, No Drawings

(56) References Cited

OTHER PUBLICATIONS

Cortesia Sanctuary et al., "How to Make Compost Tea", Mar. 22, 2013, http://www.homecompostingmadeeasy.com/composttea.html, Accessed on Jul. 12, 2016.
Norman Q. Arancon et al., "Vermicompost Tea Production and Plant Growth Impacts", Biocycle, Bd. 48, Nr. 11, Nov. 1, 2007.
Hassan Allahyari et al., "International Journal of Farming and Allied Sciences the Process of Production Compost Tea and its Use in Agriculture: A Review", Jan. 1, 2015, http://ijfas.com/wp-content/uploads/2015/03/171-176.pdf, Accessed on Jul. 12, 2016.
Maria Gomez-Brandon, "Effects of Compost and Vermicompost Teas as Organic Fertilizers", Jan. 1, 2015, www.researchgate.net/publication/270576602_Effects_of_compost_and_vermicompost_teas_as_organic_fertilisers, Accessed on Aug. 12, 2016.
Sigma-Aldrich: Microbiology Introduction. http://www.sigmaaldrich.com/analytical-chromatography/microbiology/learning-center/theory/introduction.html. Accessed on Aug. 16, 2016.

* cited by examiner

METHOD FOR PRODUCING A BIOLOGICALLY ACTIVE, MICROORGANISM-CONTAINING AQUEOUS SOLUTION OR SUSPENSION

BACKGROUND OF THE INVENTION

Technical Field

The present invention relates to a method for producing a biologically active, microorganism-containing aqueous solution or suspension.

Background Information

A large number of different microorganisms are known to inhabit our environment in a wide range of different contexts and they are even found in our bodies. For example, microorganisms are found in our digestive system.

It is also known that various natural and health processes occur which can have a positive or a negative impact on the state of the environment depending on the nature of the microorganism colony that is established as a result of environmental conditions. These various natural and health processes can have a positive or a negative impact on our health, for example, the health of our digestive system. Thus, with regards to health, it is known that taking broad-spectrum antibiotics which target disease-causing agents, also target and kill off other bacterial microorganisms, in particular those of the intestinal flora. The digestion system can initially be negatively affected until such time as an adequate balanced and healthy intestinal flora has been re-established.

It is also known that bodies of water such as wetlands, streams, pools, ponds, lakes and rivers are inhabited by very different microorganisms depending on their condition. These bodies of water may, for example, be polluted with nutrients such as phosphates or their pH value or the oxygen content may be affected. It is also known that certain microorganisms in an environment are capable of breaking down pollutants and thus improve the ecological conditions in that environment. Thus when dealing with oil pollution, for example, those bacteria which are capable of breaking up and "digesting" the long-chain hydrocarbons contained in the crude oil are frequently used. These bacteria are sprayed onto oil slicks floating on bodies of water in order to accelerate the decomposition of this toxic and environmentally hazardous substance.

SUMMARY

It is therefore desirable to obtain certain microorganisms or to obtain larger quantities of them in a targeted manner and to store them in a biologically active manner and to be able to use them.

There is a corresponding demand for methods for producing biologically active, microorganism-containing starting materials. The invention seeks to provide such a method wherein a biologically active, microorganism-containing aqueous solution or suspension is to be obtained.

According to the invention, such a method contains the steps of i) the provision of water; ii) the addition of compost in order to form a suspension; and iii) resting the suspension in an airtight environment for at least one week at a temperature of less than 15° C. Advantageous further developments of the method include that the water is boiled before being provided. Furthermore, before the step iii), and in particular between the steps i) and ii), a fine-grained mineral or organic material is added to the water and this material is mixed into the water in order to obtain a suspension. Kaolin may be used as the fine-grained mineral material. The method may also include that the water provided in step i) has a temperature of less than 15° C., and preferably has a temperature in a range from 4° C. to 10° C. The suspension is left to rest in step iii) at a temperature of 8° C. to 12° C., preferably for a period of at least one week. Furthermore, sodium chloride, in particular in the form of rock salt or sea salt, is added to the water and/or the suspension before it is left to rest. The sodium chloride is preferably added to the water immediately after step i) or immediately after the addition of a fine-grained organic or mineral material. Still further, activated charcoal, in particular beech wood charcoal, is added to the water and/or the suspension before it is left to rest. The activated charcoal is preferably added immediately before step ii). An additional treatment step makes it possible to obtain, from an already usable suspension, a modified suspension that can be used and acts in a variety of ways. In the additional step a carbohydrate-containing nutrient, in particular sugar cane molasses, is added to the suspension after step iii). The suspension is left to ferment with heat input. The suspension is left to ferment at a temperature of 25° C. to 40° C. for 5 to 10 days. In particular, the suspension is left to ferment at a temperature of 30° C. for 7 days. A possible and preferred use of a solution or suspension obtained with a method according to the invention is the improvement in the quality of bodies of water, soils, and materials by means of introduction of the suspension into the respective system.

DETAILED DESCRIPTION

In the method for producing a biologically active, microorganism-containing aqueous solution or suspension according to the invention, microorganisms contained in compost are used. By means of treatment according to the method, the quantity of the microorganisms is increased in a targeted manner or their living conditions are cultivated. The inventor has found that compost contains particularly large quantities of such microorganisms which provide a positive impact, particularly for the improvement of the environment of habitats and biotopes such as soil and bodies of water. This is particularly true of compost which is produced in a special way (see the description below for further details).

These microorganisms contained in compost are obtained according to the invention in an aqueous solution or suspension as follows:

A volume of water is provided. A fine-grained, mineral, or organic material can be introduced into the provided water. This material is then mixed into the water in order to obtain a suspension. The fine-grained material can be described in particular as kaolin or as white clay, and more rarely as kaolin clay. This particular mineral material is the kind of white-colored mineral that occurs naturally with a particularly fine grain form and round grains with a grain size of less than 2 μm. It can be added as a fine-grained material but also in the form of sawdust or similar materials. When it is added, the fine-grained mineral should be added to the water in a proportion relative to the respective volume of between 1:4 and 1:6, and particularly of 1:5.

Compost is added to the thus-obtained suspension. The quantity of the added compost (measured as a volume) should be approximately 1:1000 to 1:200 in relation to the volume of the water provided at the outset. In particular, the quantity of the added compost should be approximately 3:1000 in relation to the volume of the water provided at the outset. The vessel with the suspension contained therein is sealed in an airtight manner in order to allow the suspension to rest for a period of at least one week at a temperature of less than 15° C. while contained in an airtight environment. It is preferred that these temperatures are in a range from 8° C. to 12° C. Optimal conditions with respect to this resting at the specified temperatures are found in vaults, for example, rock-cut cellars. It is, however, also possible to realize this resting in a refrigerator, a cold storage room or a similar environment. The resting should in any case advantageously take place mostly in darkness.

At the end of this step of resting, a suspension is obtained which contains m croorganisms from the compost in a biologically active and effective quantity.

During the resting period, the fine-grained mineral material has been deposited at the base of the suspension and the aqueous portion with the microorganisms contained therein is clear and transparent. The pH value measured in test series is 7 or less than 7 and the redox potential is 200 mV or more than 200 mV. This suspension or solution can now be successfully used, and has already been used by the inventor, to obtain an improvement in environmentally-stressed biotopes, in particular bodies of water and soils. In particular, an increase in the water quality or soil quality has been obtained by applying it in the appropriate environment.

Advantageously, the water provided at the start of the method is boiled before the addition of the mineral material in order to kill off any undesirable microorganisms the water may contain. The water provided at the start of the method advantageously has a temperature of less than 15° C., in particular a temperature in a range from 4° C. to 10° C. The best results with regards to the effectiveness of the suspension or solution produced using the method according to the invention have been observed with water that has been thus temperature regulated.

Sodium chloride is preferably added to the suspension immediately after the addition of the fine-grained mineral material to the water to further increase the effectiveness. The sodium chloride is particularly in the form of rock salt or sea salt, but may also be in the form of crystal salt. The metering thereof should not be too high. An addition of salt relative to the respective volume of the originally used water in a proportion of approximately 1:2000 to approximately 3:1000 has proven to be suitable. In particular, the addition of salt relative to the respective volume of the originally used water in a proportion of approximately 3:2000 has proven to be suitable.

A portion of activated charcoal is another possible addition to the suspension. The addition of the activated charcoal preferably occurs immediately before the addition of compost to the suspension. The activated charcoal may be beech wood charcoal. Here too it has been found that a small quantity of this material produces an improvement of the biologically active, microorganism-containing aqueous solution obtained with the method. In this case, an addition of activated charcoal relative to the volume of originally provided water in the order of 1:10000 to 1:1000 has proven to be effective. In particular, addition of activated charcoal relative to the volume of originally provided water in the order of 5:10000 has proven to be effective. The activated charcoal, which preferably is beech wood charcoal, should be of pharmaceutical quality.

As has already been mentioned, a solution is obtained using the above described procedures. The solution above the deposited mineral sediment is clear and transparent and already contains microorganisms in a biologically active quantity and can be used in this form.

In another method step this solution or suspension can be further treated in order to obtain a useable modified alternative or additional variant of a biologically active, microorganism-containing aqueous solution or suspension. This step involves opening the suspension-containing vessel after resting the suspension in an airtight environment, the addition of a carbohydrate-containing nutrient to the suspension, and leaving the suspension to ferment with heat input. The carbohydrate-containing nutrient can be sugar cane molasses, for example. This fermentation process occurs anaerobically.

The suspension is left to ferment at a temperature of 25° C. to 40° C. The suspension is preferably left to ferment at a temperature of 30° C. The fermentation duration is 5 to 10 days. The fermentation duration preferably is 7 days.

As already stated, at the end of the fermentation process one obtains a variant compared with the already biologically active and useable microorganism-containing aqueous solution obtainable with the first method steps. The variant has a different composition of microorganisms. Measurements undertaken by the inventor using exemplary embodiments have shown that this solution has a lower pH value than the solution obtained after the first method step. The lower pH value is a pH≤4. The determined redox potential of ≤−200 mV is also very different to that of the solution or suspension which is obtained after the first method steps.

For a specific additional, application-related formulation, further additives such as essences or the like can be added to the solution obtained with the method according to the invention. The further additives can be added either during the production process or after the step of resting. If appropriate, the additives can be added after the fermentation step.

After resting the solution is clear and transparent. After the fermentation process the solution is turbid due to the carbohydrate-containing nutrients therein. The inventor has succeeded in significantly improved the water quality of unbalanced bodies of water that were in a critical ecological state by means of the introduction of solutions obtained according to the invention after the resting stage or after the fermentation process. The thus-introduced microorganisms were able to break down harmful substances contained in the environment of the body of water and thus significantly increase the water quality. Improved yields have also been obtained from cultivated plants when the soil in which they were cultivated has been treated with the suspension according to the invention in either of the two variant forms. Applications in humans, e.g. in external applications or internal administration, are also conceivable. Applications such as the concomitant treatment of skin diseases such as neurodermatitis with the suspension according to the invention may be possible.

The method according to the invention is explained in further detail below with reference to an exemplary formulation.

A first variant of a biologically active, microorganism-containing aqueous solution or suspension according to the invention was obtained as follows:

10 liters of water of drinking water quality were brought to boil, and left to simmer gently for approximately 10 minutes, and then cooled. After cooling to room temperature, the water was cooled in an appropriate manner, e.g. in a refrigerator, to a temperature of between 4° C. and 10° C. and was then poured into a glass bottle that can hold this volume. Fine-grained kaolin was then added at a volume of 2 liters to the water. The obtained composition was mixed thoroughly to produce a suspension. Sodium chloride in the form of crystal salt was then mixed in at a volume of 14 ml. Rock salt or sea salt may be used instead of crystal salt. In a subsequent step, finely ground beech wood charcoal of pharmaceutical quality and at a volume of 5 ml was mixed into the suspension. Finally, compost was mixed in at a volume of 28 ml. The glass vessel was sealed in an airtight manner and the mixture was left to rest with the vessel being stored in a cool atmosphere at 8° C. to 12° C., and with a maturation in the form of a cold fermentation taking place.

A compost produced specifically for this production process was used as the compost, the production of which is again described separately below.

At the end of the above-described method, after the resting, a clear aqueous solution was obtained above the deposited kaolin sediment. The obtained, solution proved to be biologically active and contained microorganisms. The pH value of this solution was 7 or less than 7 and a measured redox potential of more than 200 millivolts was determined. This solution could be easily stored over longer periods of time and was suitable for introduction of the microorganisms contained therein into stressed habitats, in particular bodies of water, in order to facilitate the breakdown of harmful components and improve the quality of the habitats.

From this solution, a further variant of a solution or suspension according to the invention can be produced in accordance with a further development of the method according to the formulation described below. For this purpose, 12 liters of the suspension produced in the first method (i.e. including the kaolin) was used as a starting material. To this quantity of suspension, sugar cane molasses, in particular organically grown sugar cane molasses, was added at a quantity of 200 ml. This suspension was mixed thoroughly by means of agitation or stirring. The vessel containing this suspension was sealed with a fermentation bung and placed in the water bath of a fermenter. The water of the water bath was maintained at a temperature of 30° C. and this mixture was left to ferment for seven days.

At the end of the fermentation process a turbid and brown-colored aqueous solution or suspension was obtained. The obtained solution or suspension had a significantly lower pH value of pH<4 and a measured redox potential of approximately −200 mV. This solution also proved to be very effective in applications for improvement of habitats, in particular bodies of water, in that the specific microorganisms contained therein accelerated the breakdown of pollutants and thus supported an ecologically stable environment.

The solutions or suspensions obtained according to the above-described exemplary embodiments achieved good results, both when used separately or in combination.

A preferred option for producing the compost used in the above-described method shall now be described. This compost can also be used completely separately from the suspension produced according to the method according to the invention, so that its production and also its use are themselves to be seen as autonomous inventions.

The production of the compost consists of a fermentation instead of a rotting process which is commonly encountered elsewhere. The fact that here the starting materials are transformed by means of fermentation is of critical importance because it is only in this manner that the desired microorganism fauna is obtained. A different and unfavorable microfauna is formed during rotting.

The fermentation compost can be produced in seven steps as follows:

Plant and animal waste (e.g. kitchen and slaughter waste) are cold fermented at 10-20° C. in an airtight environment after the addition of microorganisms. Preferably the plant and animal waste is cold fermented in accordance with the so-called Bokashi method.

Additional plant and animal raw materials are collected. This additional plant and animal raw material includes organic material and fecal material.

Water is added to the additional plant and animal raw materials in order to create a well-moistened mixture but without liquefying said mixture.

The material obtained in the first step and the moistened mixture of the additional plant and animal raw materials are combined and injected with an addition of mature fermentation compost. The mature fermentation compost may particularly be of the sort produced according to this method.

The thus-obtained starting material is layered in a heap. The heap may have a bell shape, a spherical segment shape, or a rounded conical shape.

The fermentation which now commences is controlled by means of adjustment of the air and water input in such a way that it takes place at around 65° C., i.e., such that the core temperature in the heap is approximately 65° C.

The compost is now left to mature for a maturation period of approximately 6 months and is turned over multiple times during this period:

Once the heap has been built, the temperature in the material increases after a few days to approximately 65° C. After a certain period of time the temperature falls.

When the compost is below a temperature of 55° C. after approximately 3 weeks, the heap is turned for the first time. The temperature then rises again and the temperature of approximately 65° C. is reached for a second time, and here too the temperature falls again after a certain period of time.

When the compost is then below the temperature of 40° C., it is turned a second time.

A third turning takes place when the temperature in the heap is below 30° C.

A fourth turning takes place when the temperature in the heap is below 25° C.

The fermentation compost is mature when its temperature approaches normal soil temperature and a constant temperature of between 8° C. and 16° C. has been established. This generally occurs after the fourth turning of the heap.

The organic material in the heap should be very thoroughly mixed together and should, as far as possible, have a variety of constituents made up of various parts of the living organisms from which they are derived. The following empirical formula is generally applied: The more homogenous the mixture and the more biodiverse the range of organic material, the better the result. However, disease-affected organic waste, such as green waste from disease-affected plants, or contaminated constituents should be introduced into the center of the heap. As has already been stated, it is important that the compost is fermented. This occurs at temperatures of at least 55° C. and in particular at 65° C. At these temperatures the so-called hot fermentation takes place. (The hot fermentation may also be called the mesothermal phase.) The fact that the organic material is composted by means of fermentation processes and is not involved in any rotting processes is therefore of particular importance in this procedure. This is because it is funguses that play the decisive role in the transformation process here. In these conditions those kinds of aerobic organisms exist that produce antibiotically effective materials capable of reliably destroying harmful organisms such as worm eggs, disease-causing germs and even spore-forming organisms such as anthrax spores. That is why a temperature of 55° C. or higher, in particular 65° C., must be reached in the heap before it is turned for the first time. This typically occurs a few days after the first building of the heap and this temperature must be maintained for at least three weeks and monitored with temperature measurement.

The effect is further improved when a tube is inserted approximately centrally and extending vertically into the compost heap. The tube is inserted for the purpose of aeration. The flue effect ensures that greater aeration of the organic material and appropriate nourishment of the aerobic microorganisms are achieved here. The inventor was able to obtain particularly good results here with a tube the length of which was adapted to the frequency range of the so-called earth frequency, also referred to as the earth's tone. This frequency is 68,051 Hz after multiple octave transpositions. The tube, for this purpose, was divided into various lengths by means of cross-sectional tapering. The length of this tube was 2329 mm. The external diameter of the tube, which need not be dimensioned exactly so in order to achieve the effect, was 140 mm with a wall thickness of 12.7 mm. The tube was formed from polyethylene (PE), particularly from PEHD. The division of the various chambers formed by the cross-sectional tapering was then as follows:

A bottom chamber introduced into the compost with side openings in the tube wall was 348 mm long. All of the adjoining chambers were 229, 313, 229, 439, 229, 313, and 229 mm long in that order and without breaches in the tube wall. The tube was thus attuned to the harmonic overtones of the earth's tone.

The formulations presented above as exemplary embodiments are purely descriptive and do not limit the scope of the invention.

The invention claimed is:

1. A method for producing a biologically active, microorganism-containing aqueous solution or suspension comprising the following steps:
   (i) providing water;
   (ii) adding compost, made with organic matter transformed by a cold fermentation at a temperature of 10-20° C. according to the Bokashi method, to the water in order to form a suspension;
   (iii) resting the suspension for maturation via fermentation in an airtight environment for at least one week at a temperature of less than 15° C.

2. The method according to claim 1, (iii) wherein the water is boiled before being provided.

3. The method according to claim 1, wherein before the step iii), a fine-grained mineral or organic material is added to the water and this material is mixed into the water in order to obtain a suspension.

4. The method according to claim 3, wherein kaolin is used as the fine-grained mineral material.

5. The method according to claim 3, wherein the fine-grained mineral or organic material is added to the water between the steps i) and ii) and then this material is mixed into the water.

6. The method according to claim 1, wherein the water provided in step i) has a temperature of less than 15° C.

7. The method according to claim 6, wherein the water provided in step i) has a temperature in a range of about 4° C. to about 10° C.

8. The method according to claim 1 wherein the suspension is left to rest in step iii) at a temperature of 8° C. to 12° C.

9. The method according to claim 1, wherein sodium chloride is added to the water and/or the suspension before it is left to rest.

10. The method according to claim 1, wherein activated charcoal is added to the water and/or the suspension before it is left to rest.

11. The method according to claim 10, wherein the activated charcoal is beech wood charcoal.

12. The method according to claim 10, wherein the activated charcoal is added to the water and/or the suspension immediately before step ii).

13. The method according to claim 1, wherein a carbohydrate-containing nutrient is added to the suspension after step iii), and the suspension containing the carbohydrate-containing nutrient is left to ferment with heat input.

14. The method according to claim 13, wherein the suspension containing the carbohydrate-containing nutrient is left to ferment at a temperature of 25° C. to 40° C.

15. The method according to claim 13, wherein the carbohydrate-containing nutrient is sugar cane molasses.

16. A method for producing a biologically active, microorganism-containing aqueous solution or suspension comprising the following steps:
   providing water;
   adding compost, made with organic matter transformed by a fermentation according to the Bokashi method, to the water in order to form a suspension in an amount of 1 part compost and 200 parts to 1000 parts water both measured as a volume;
   resting the suspension for maturation via fermentation in an airtight environment for at least one week at a temperature of less than 15° C.

17. The method according to claim 16, wherein before the resting step, a fine-grained mineral or organic material is added to the water and this material is mixed into the suspension.

18. The method according to claim 16, wherein a carbohydrate-containing nutrient is added to the suspension after the resting step, and the suspension containing the carbohydrate-containing nutrient is left to ferment with heat input.

19. The method according to claim 16, wherein the water is boiled before being provided, and wherein sodium chloride is added to the water and/or the suspension before it is left to rest.

20. A method for producing a biologically active, microorganism-containing aqueous solution or suspension comprising the following steps:
   (i) boiling water and then providing the water;
   (ii) adding compost, made with organic matter transformed by fermentation, to the water in order to form a suspension; and
   (iii) resting the suspension in an airtight environment for at least one week at a temperature of less than 15° C.;
   wherein sodium chloride is added to the water and/or the suspension before it is left to rest.

* * * * *